(12) United States Patent
Zhou et al.

(10) Patent No.: US 12,357,698 B1
(45) Date of Patent: Jul. 15, 2025

(54) FUS PROTEOLYSIS-TARGETING CHIMERA, PREPARATION METHOD AND APPLICATIONS THEREOF

(71) Applicant: SHANDONG NORMAL UNIVERSITY, Jinan (CN)

(72) Inventors: Jun Zhou, Jinan (CN); Songbo Xie, Jinan (CN)

(73) Assignee: SHANDONG NORMAL UNIVERSITY, Jinan (CN)

( * ) Notice: Subject to any disclaimer, the term of this patent is extended or adjusted under 35 U.S.C. 154(b) by 0 days.

(21) Appl. No.: 19/073,405

(22) Filed: Mar. 7, 2025

(30) Foreign Application Priority Data

Sep. 10, 2024 (CN) .......................... 202411258878.5

(51) Int. Cl.
  *C12N 15/115*  (2010.01)
  *A61K 47/54*   (2017.01)
  *A61K 47/69*   (2017.01)

(52) U.S. Cl.
  CPC ........ *A61K 47/549* (2017.08); *A61K 47/6921* (2017.08); *C12N 15/115* (2013.01); *C12N 2310/16* (2013.01)

(58) Field of Classification Search
  None
  See application file for complete search history.

(56) References Cited

FOREIGN PATENT DOCUMENTS

| CN | 116179554 A | * | 5/2023 | ......... A61K 41/0057 |
| WO | WO-2021221784 A2 | * | 11/2021 | ........... C12N 15/115 |

OTHER PUBLICATIONS

Assoni et al., Stem Cell Rev Rep. Apr. 2023; 19(3):625-638. doi: 10.1007/s12015-022-10489-8. Epub Dec. 14, 2022. PMID: 36515764.*
Bekes et al., Nat Rev Drug Discov. Mar. 2022;21(3):181-200. doi: 10.1038/s41573-021-00371-6. Epub Jan. 18, 2022. PMID: 35042991.*
Xu and Ellington, "Anti-peptide aptamers recognize amino acid sequence and bind a protein epitope" Proc Natl Acad Sci U S A. Jul. 23, 1996;93(15):7475-80. doi: 10.1073/pnas.93.15.7475. PMID: 8755498 PMCID: PMC38769.*

* cited by examiner

*Primary Examiner* — Michael Szperka
(74) *Attorney, Agent, or Firm* — IPRO, PLLC

(57) ABSTRACT

The present invention belongs to the technical field of proteolysis-targeting chimera preparation and biomedical technology, and specifically relates to a FUS proteolysis-targeting chimera, preparation method and applications thereof. Specifically, the present invention designed ligands specifically binding to FUS based on the "GGUG" RNA motif that specifically binds to FUS, and developed FUS proteolysis-targeting chimeras that specifically degrade wild-type and mutant FUS by connecting CRBN ligands at their 5' end. Meanwhile, to ensure effective action of FUS proteolysis-targeting chimeras in the brain, the present invention designed DNA nanoflowers based on transferrin receptor aptamers, which can effectively load FUS proteolysis-targeting chimeras and deliver them to the brain for action, achieving precise medicine for ALS patients with FUS mutations.

7 Claims, 15 Drawing Sheets
Specification includes a Sequence Listing.

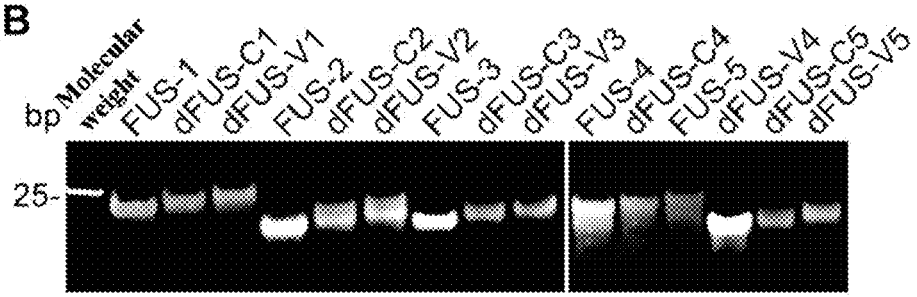
FIG. 7A
FIG. 7B
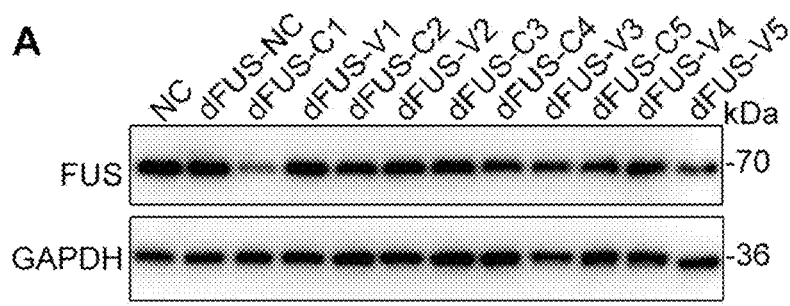
FIG. 8A
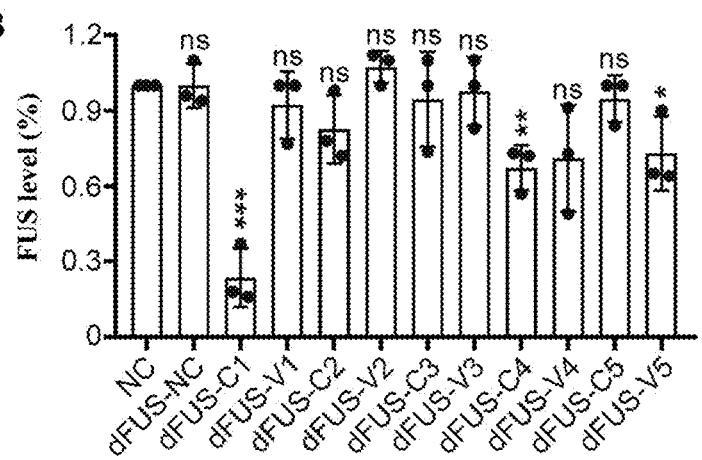
FIG. 8B

A

B

```
SEQUENCE LISTING

Sequence total quantity: 9
SEQ ID NO: 1            moltype = RNA  length = 20
FEATURE                 Location/Qualifiers
source                  1..20
                        mol_type = other RNA
                        organism = synthetic construct
SEQUENCE: 1
gtttggtgat gtttggtgat                                                    20

SEQ ID NO: 2            moltype = RNA  length = 20
FEATURE                 Location/Qualifiers
source                  1..20
                        mol_type = other RNA
                        organism = synthetic construct
SEQUENCE: 2
ttggcattga atttggtgta                                                    20

SEQ ID NO: 3            moltype = RNA  length = 20
FEATURE                 Location/Qualifiers
source                  1..20
                        mol_type = other RNA
                        organism = synthetic construct
SEQUENCE: 3
ttgtgagttt accgggtgta                                                    20

SEQ ID NO: 4            moltype = RNA  length = 20
FEATURE                 Location/Qualifiers
source                  1..20
                        mol_type = other RNA
                        organism = synthetic construct
SEQUENCE: 4
ttttgaagga gggtgaaggg                                                    20

SEQ ID NO: 5            moltype = RNA  length = 20
FEATURE                 Location/Qualifiers
source                  1..20
                        mol_type = other RNA
                        organism = synthetic construct
SEQUENCE: 5
ttgcgtatca tatggtgtgg                                                    20

SEQ ID NO: 6            moltype = RNA  length = 20
FEATURE                 Location/Qualifiers
source                  1..20
                        mol_type = other RNA
                        organism = synthetic construct
SEQUENCE: 6
gtttgctgat gtttgctgat                                                    20

SEQ ID NO: 7            moltype = DNA  length = 22
FEATURE                 Location/Qualifiers
source                  1..22
```

```
                        mol_type = other DNA
                        organism = synthetic construct
SEQUENCE: 7
gaaggcgtgg taccacgctt tc                                            22

SEQ ID NO: 8            moltype = DNA  length = 58
FEATURE                 Location/Qualifiers
source                  1..58
                        mol_type = other DNA
                        organism = synthetic construct
SEQUENCE: 8
tggtaccacg ccttcgtttg gtgatgtttg gtgataaaaa aaaaaaaaaa agaaagcg     58

SEQ ID NO: 9            moltype = DNA  length = 22
FEATURE                 Location/Qualifiers
source                  1..22
                        mol_type = other DNA
                        organism = synthetic construct
SEQUENCE: 9
aggcgtggta ccacgctttc tt                                            22
```

FUS PROTEOLYSIS-TARGETING CHIMERA, PREPARATION METHOD AND APPLICATIONS THEREOF

REFERENCE TO SEQUENCE LISTING

The instant application contains a Sequence Listing in XML format as a file named "PCPIP202504US Sequence Listing.xml", created on Mar. 3, 2025, of 9,079 bytes in size, and which is hereby incorporated by reference in its entirety.

CROSS-REFERENCE TO RELATED APPLICATIONS

The present invention claims priority benefit of Chinese Patent Application No. 202411258878.5, filed 10 Sep. 2024, the entirety of each of the above-mentioned patent application is hereby incorporated by reference herein and made a part of this specification, for all purpose.

TECHNICAL FIELD

The present invention belongs to the technical field of proteolysis-targeting chimera (PROTAC) preparation and biomedical technology, and specifically relates to a FUS PROTAC, preparation method and applications thereof.

BACKGROUND OF THE INVENTION

Amyotrophic lateral sclerosis (ALS) is a severe neurodegenerative disease characterized by premature degeneration of motor neurons, leading to progressive, fatal paralysis, typically resulting in death within 3 years of symptom onset. FUS gene mutations cause 4% of familial amyotrophic lateral sclerosis and 1% of sporadic amyotrophic lateral sclerosis. FUS is a multifunctional DNA/RNA binding protein composed of 526 amino acids that participates in RNA metabolism, including RNA transcription, splicing, transport, translation, and degradation. Under physiological conditions, FUS is primarily localized in the nucleus, while mutant FUS accumulates in the cytoplasm in granular, filamentous, or dense forms. Most mutations found in ALS patients are clustered in glycine-rich regions and the extreme C-terminal region of the protein, including P525L, R521C, R521G, and R521H, etc. Mutations in the 3' untranslated region of the FUS gene have also been reported in ALS patients, with the large accumulation of FUS found in the nucleus and cytoplasm of mutant 3'UTR FUS fibroblasts indicating a mechanism of translational dysregulation. This series of FUS mutations can induce disease through either gain of function in the cytoplasm or loss of function in the nucleus. ALS treatment is primarily supportive, including physical therapy, nutritional support, and mechanical ventilation in later stages. Currently, the only available drug treatment is Riluzole, which shows only modest survival benefits in clinical trials, highlighting the urgent need for new therapeutic approaches for ALS.

Proteolysis-Targeting Chimeras (PROTACs) are bifunctional small molecules comprising two functional ligands and a linker: one ligand binds to the protein of interest (POI), while the other binds to an E3 ubiquitin ligase. When both ends of the PROTAC simultaneously bind to the target protein and E3, the target protein is tagged with ubiquitin and subsequently degraded by the ubiquitin-proteasome system. However, the inventors found that no PROTACs targeting FUS protein degradation have been reported to date.

Additionally, the delivery of central nervous system disease therapeutics to the brain is typically limited by the blood-brain barrier (BBB). Receptors highly expressed on blood-brain barrier endothelial cell surfaces include transferrin receptor (TfR), insulin receptor, and low-density lipoprotein receptor. Utilizing these surface receptors to mediate drug transport across the blood-brain barrier is a promising strategy. Studies have shown that using aptamers targeting the transferrin receptor as carriers can enhance the blood-brain barrier penetration of nucleic acid drugs. Nucleic acid nanomaterials possess good biocompatibility, biodegradability, and programmability, with important applications in the biomedical field. Rolling circle amplification is an isothermal enzymatic nucleic acid amplification technique used for large-scale production of nucleic acid nanomaterials with pre-designed desired structures and functions, such as DNA nanoflowers, DNA origami, and nanotubes. However, the inventors found that there are currently no reports on developing DNA nanoflower carriers using transferrin receptor-targeting aptamers for brain delivery.

SUMMARY OF THE INVENTION

Addressing the aforementioned problems in the existing technology, the inventors, through long-term technical and practical exploration, provide a FUS proteolysis-targeting chimera (PROTAC), preparation method and applications thereof. Specifically, the present invention designed, synthesized, and screened chimeras that efficiently degrade wild-type FUS and its mutant proteins. Furthermore, the present invention constructed a DNA nanoflower delivery carrier based on transferrin receptor aptamers, achieving brain delivery of FUS PROTAC. Based on the above research findings, the present invention was completed.

To achieve the above technical objectives, the present invention adopts the following technical solutions:

in a first aspect, the present invention provides a FUS proteolysis-targeting chimera (PROTAC) with a general structure: F-E;

wherein F is an aptamer specifically binding to FUS protein; E is a ligand for E3 ubiquitin ligase.

Wherein, the FUS protein is human-derived and can be wild-type FUS protein or mutant FUS protein, wherein the mutant FUS protein includes FUS mutant proteins that mediate human amyotrophic lateral sclerosis.

Nucleotide sequences of the aptamers specifically binding to FUS protein are shown in SEQ ID NOs: 1-5.

In a second aspect, the present invention provides a method for preparing the above FUS proteolysis-targeting chimera, comprising:

synthesizing single-stranded RNA with azide modification and terminally alkyne-modified E3 ubiquitin ligase ligand, and coupling the single-stranded RNA with azide modification and the terminally alkyne-modified E3 ubiquitin ligase ligand through click reaction.

Further, the azide modification is at the 5' end of the single-stranded RNA, specifically connected to the 5' terminus of the single-stranded RNA through a C6 amino phosphoramidite monomer.

In a third aspect, the present invention provides an application of the FUS proteolysis-targeting chimera in preparing DNA nanoflowers based on transferrin receptor aptamers.

In a fourth aspect, the present invention provides a DNA nanoflower based on transferrin receptor aptamers, wherein the DNA nanoflower is loaded with the above FUS proteolysis-targeting chimera. Specifically, the DNA nanoflower utilizes transferrin receptor-targeting aptamers and rolling circle amplification technology to penetrate the blood-brain barrier, while using base complementarity principles to load the FUS proteolysis-targeting chimera onto the DNA nanoflower carrier, thereby delivering the FUS proteolysis-targeting chimera to the brain to degrade wild-type and mutant FUS proteins to alleviate and treat amyotrophic lateral sclerosis.

In a fifth aspect, the present invention provides applications of the above FUS proteolysis-targeting chimera or DNA nanoflower based on transferrin receptor aptamers in preparing products.

The products have at least one or more of the following effects:
 (a) degradation of FUS protein;
 (b) treatment of amyotrophic lateral sclerosis.

In a sixth aspect, the present invention provides a pharmaceutical composition comprising, as an active ingredient, at least the above FUS proteolysis-targeting chimera or DNA nanoflower based on transferrin receptor aptamers. The pharmaceutical composition can be used to degrade FUS protein and thereby treat amyotrophic lateral sclerosis.

In a seventh aspect, the present invention provides a method for treating amyotrophic lateral sclerosis, comprising administering to a subject a therapeutically effective amount of the above FUS proteolysis-targeting chimera, DNA nanoflower based on transferrin receptor aptamers, or pharmaceutical composition.

It should be noted that while the above technical solutions focus on the FUS proteolysis-targeting chimera and further construct DNA nanoflowers based on transferrin receptor aptamers that can effectively cross the blood-brain barrier for treating ALS, based on the inventive concept of the present invention, utilizing other nucleic acid-PROTAC, antisense oligonucleotides (ASO), siRNA drugs, etc. to achieve brain targeting for treating amyotrophic lateral sclerosis and other related diseases also falls within the scope of protection of this application.

Compared with existing technical solutions, the above one or more technical solutions have the following beneficial effects:
 the above technical solutions are based on the specific binding of the "GGUG" RNA motif to FUS, designing ligands that specifically bind to FUS, and developing PROTACs that specifically degrade wild-type and mutant FUS by connecting Cereblon (CRBN) ligands at their 5' end. Meanwhile, to ensure effective action of PROTACs in the brain, the above technical solutions designed DNA nanoflowers based on transferrin receptor aptamers, which can effectively load PROTACs and deliver them to the brain for action, achieving precise medicine for ALS patients with FUS mutations.

Through experimental verification, the RNA-based PROTACs involved in the above technical solutions demonstrate good degradation efficiency and mitigation of neurotoxicity caused by FUS overexpression in vitro, while in vivo, the nanoflowers can effectively deliver PROTACs to the brain and exert FUS protein degradation function, showing good practical application value in treating ALS caused by FUS mutations.

BRIEF DESCRIPTION OF DRAWINGS

The accompanying drawings forming part of the present invention are used to provide further understanding of the present invention, and the schematic embodiments of the present invention and the description thereof are used to explain the present invention and do not constitute an undue limitation of the present invention. Hereinafter, embodiments of the present invention are described in detail in connection with the accompanying drawings, wherein:

FIG. 7A~B shows the non-denaturing SDS-PAGE results demonstrating the electrophoresis results before and after connecting different azide-modified RNA ligands with CRBN ligand or von Hippel-Lindau (VHL) ligand in Example 1, wherein FIG. 7A shows different azide-modified RNA sequence information, and FIG. 7B shows electrophoresis results confirming successful connection of different RNA sequences with CRBN or VHL ligands.

FIG. 8A~B shows the degradation effects of 10 PROTACs on FUS in PC12 cells in Example 2, FIG. 8A shows the electrophoresis results of FUS degradation by 10 PROTACs, FIG. 8B shows the quantitative statistics of A.

FIG. 9A~B shows the molecular docking results of dFUS-C1 binding with FUS protein and CRBN ligand in Example 3, wherein FIG. 9A shows the molecular docking diagram of dFUS-C1 binding with FUS protein and CRBN ligand, FIG. 9B shows the specific amino acid sites of dFUS-C1 binding with FUS and CRBN.

FIG. 10A~C shows the concentration-dependent degradation effects of dFUS-C1 on FUS in PC12 and SH-SY5Y cells and proteomics results before and after dFUS-C1 treatment in Example 3, wherein FIG. 10A shows the concentration-dependent degradation effects of dFUS-C1 on FUS in PC12 and SH-SY5Y cells, FIG. 10B shows the quantitative statistics of FIG. 10A, FIG. 10C shows the proteomics results before and after dFUS-C1 treatment.

FIG. 11A~E shows the concentration-dependent degradation effects of dFUS-C1 on mutant FUS in Example 4; wherein FIG. 11A shows wild-type FUS (FUS-WT), FIG. 11B shows mutant FUS-P525L, FIG. 11C shows mutant FUS-R521C, FIG. 11D shows mutant FUS-R521G, FIG. 11E shows mutant FUS-R521H.

FIG. 12A shows detection of reactive oxygen species content in SH-SY5Y cells, FIG. 12B shows detection of lactate dehydrogenase release content in SH-SY5Y cells, FIG. 12C shows detection of SH-SY5Y cell viability.

FIG. 14A shows the serum stability test results of dFUS-C1 and dFUS-PS at the indicated times, FIG. 14B shows the quantitative statistics of FIG. 14A, FIG. 14C shows the dose-dependent FUS degradation effect of dFUS-PS, FIG. 14D shows the quantitative statistics of C.

FIG. 16A~C shows the results of DNA nanoflowers successfully loading dFUS-PS in Example 7, wherein FIG. 16A shows the 620-700 nm fluorescence spectral scanning before and after loading PROTAC nanoflowers, FIG. 16B shows the particle size analysis before and after loading PROTAC nanoflowers, FIG. 16C shows the scanning electron microscopy images before and after loading PROTAC nanoflowers, with scale bar of 300 nm.

FIG. 17A shows the in vivo and ex vivo imaging at the indicated times after tail vein injection of NF@Cy5-dFUS-PS, FIG. 17B shows the fluorescence staining of mouse brain sections after tail vein injection of NF@Cy5-dFUS-PS.

DETAILED DESCRIPTION

Figure 1:
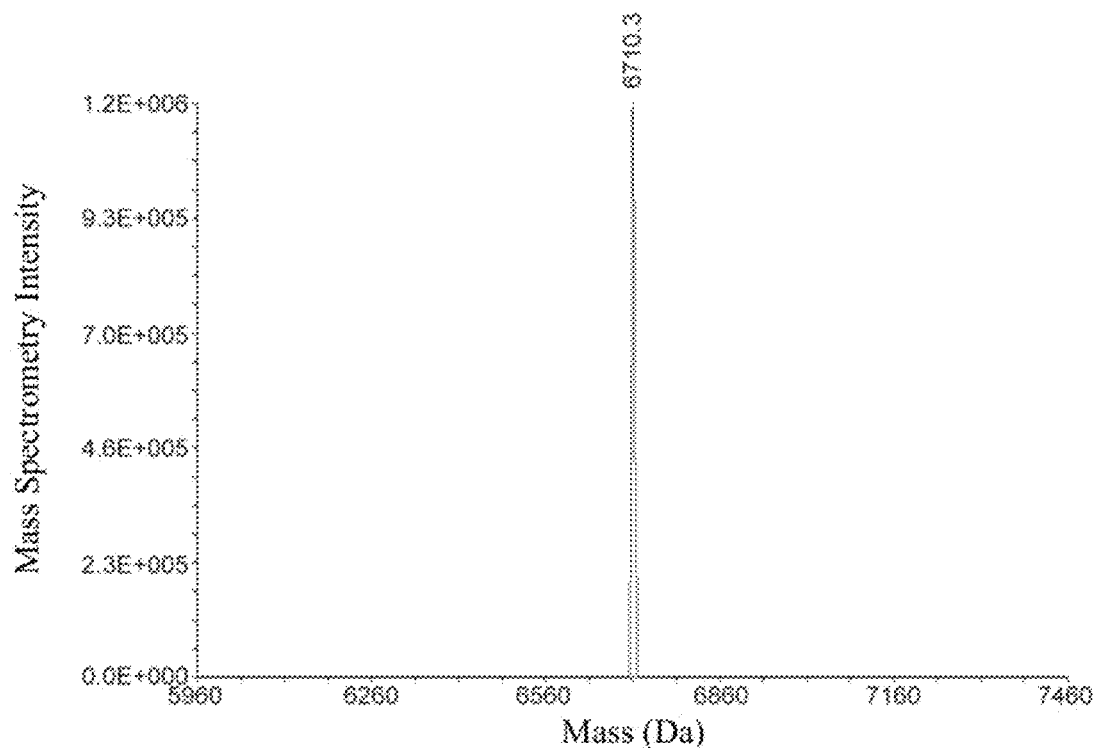
FIG. 1 shows the mass spectrometry results of $N_3$-FUS-RNA #1 with 5' azide modification synthesized in Example 1 of the present invention.
Figure 2:
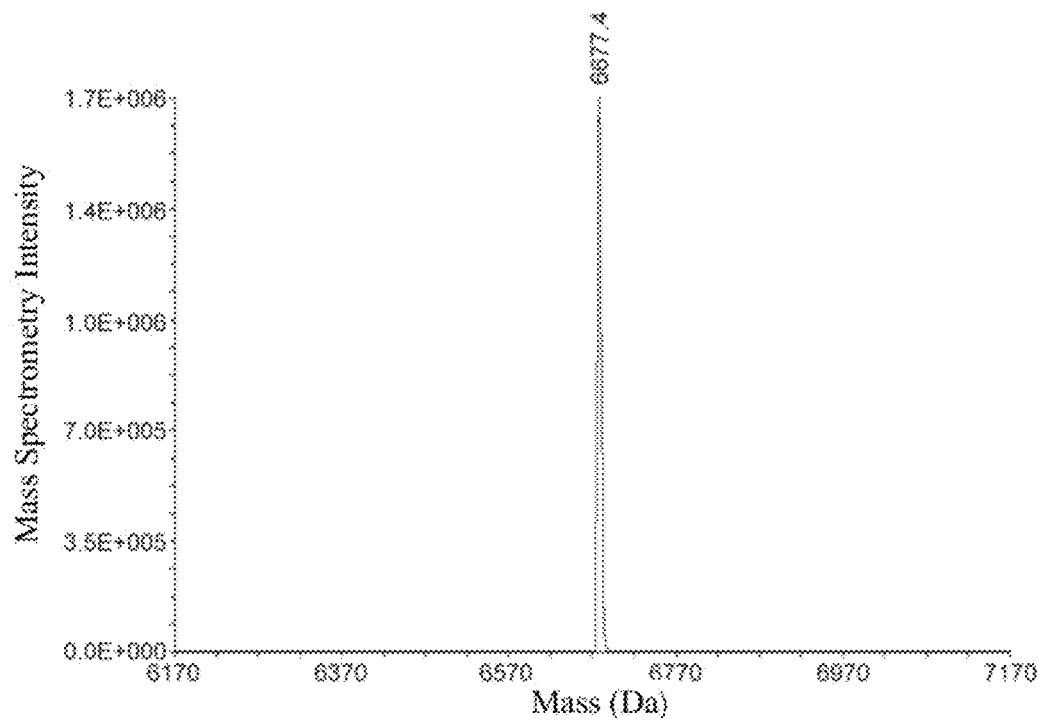
FIG. 2 shows the mass spectrometry results of $N_3$-FUS-RNA #2 with 5' azide modification synthesized in Example 1 of the present invention.
Figure 3:
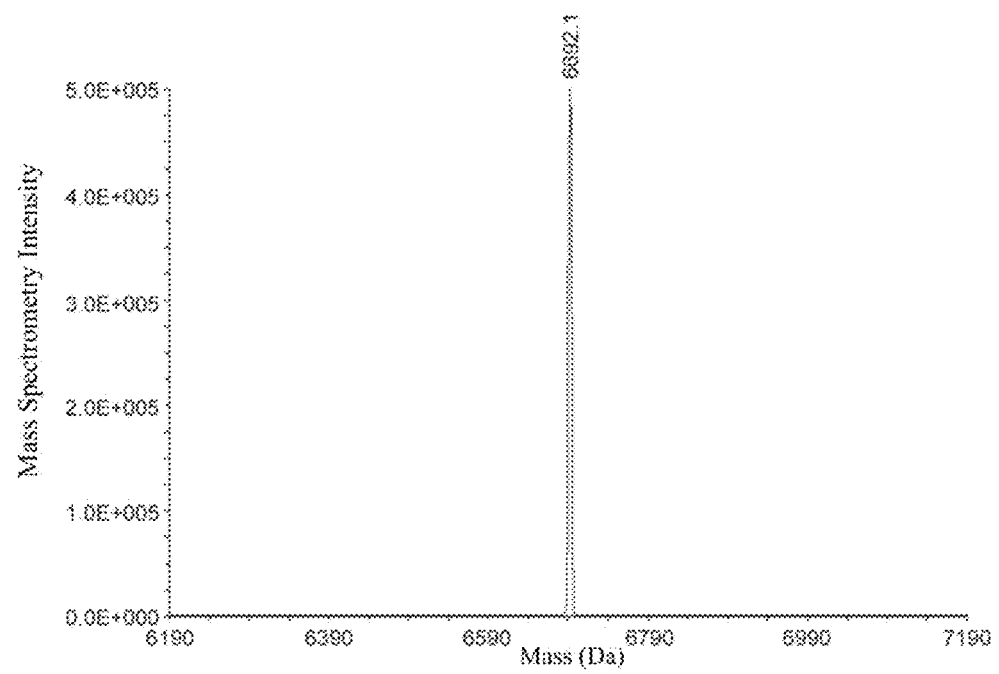
FIG. 3 shows the mass spectrometry results of $N_3$-FUS-RNA #3 with 5' azide modification synthesized in Example 1 of the present invention.
Figure 4:
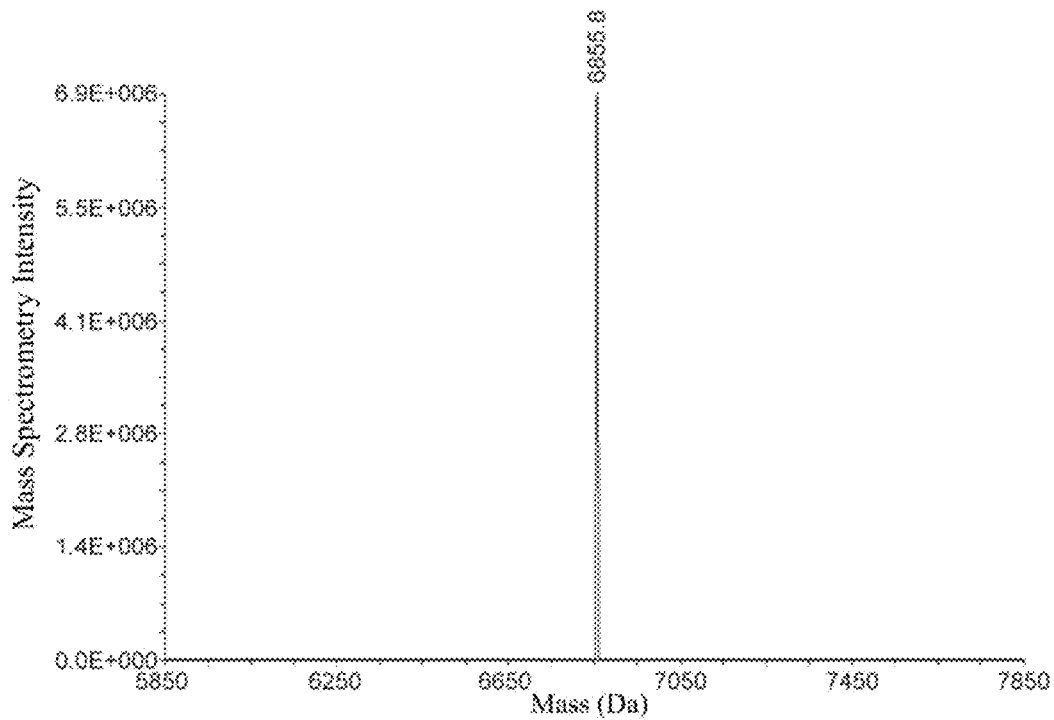
FIG. 4 shows the mass spectrometry results of $N_3$-FUS-RNA #4 with 5' azide modification synthesized in Example 1 of the present invention.
Figure 5:
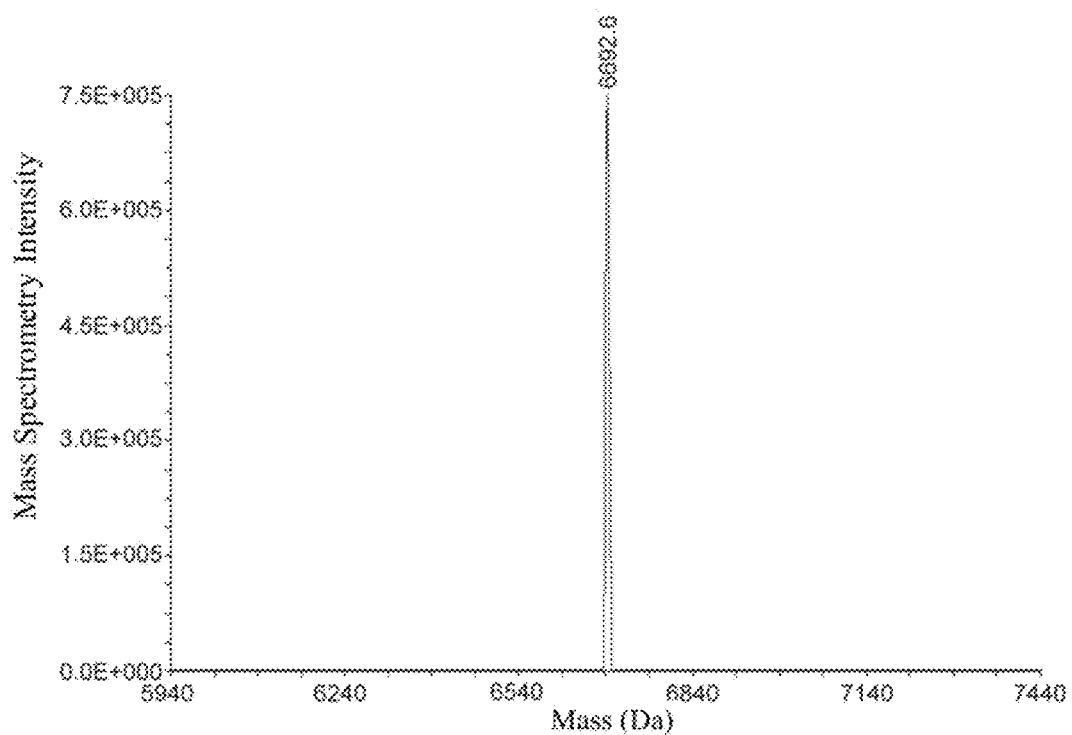
FIG. 5 shows the mass spectrometry results of $N_3$-FUS-RNA #5 with 5' azide modification synthesized in Example 1 of the present invention.
Figure 6:
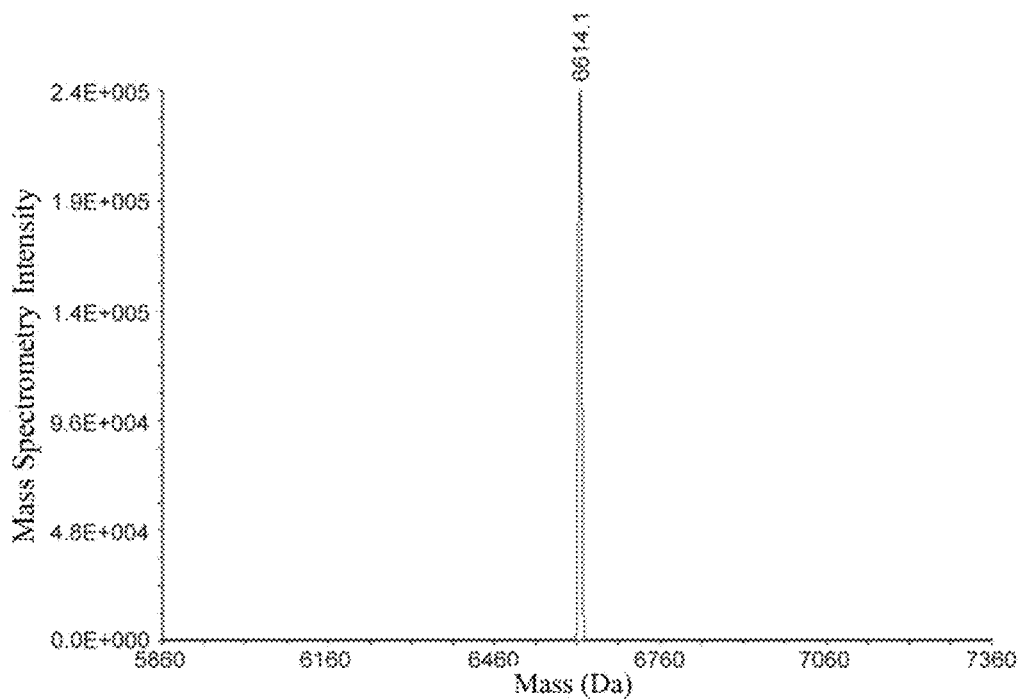
FIG. 6 shows the mass spectrometry results of $N_3$-FUS-RNA #NC with 5' azide modification synthesized in Example 1 of the present invention.

It should be noted that the following detailed descriptions are all illustrative and intended to provide further clarification of the present invention. Unless otherwise indicated, all technical and scientific terms used herein have the same meaning as commonly understood by one of ordinary skill in the art to which the present application belongs.

It is important to note that the terms used here are for describing specific embodiments and are not intended to limit the exemplary embodiments of the present invention. As used herein, the singular form is intended to include the plural form as well, unless the context clearly indicates otherwise, and it should also be understood that when the terms "comprising" and/or "including" are used in this specification, they indicate the presence of features, steps, operations, devices, components, and/or combinations thereof.

As mentioned above, mutations in the FUS gene cause 4% of familial amyotrophic lateral sclerosis and 1% of sporadic amyotrophic lateral sclerosis, and there are no good treatment methods to date. Furthermore, the presence of the blood-brain barrier prevents most drugs from exerting their effects in the brain. PROTACs have the function of specifically degrading proteins, therefore using nanoflowers to load PROTACs to penetrate the blood-brain barrier and degrade wild-type and mutant FUS to alleviate and treat ALS is a feasible approach.

Based on the specific binding of the "GGUG" RNA motif to FUS, the present invention designed ligands that specifically bind to FUS, and developed PROTACs that specifically degrade wild-type and mutant FUS by connecting CRBN ligands at their 5' end. To ensure effective action of PROTACs in the brain, the present invention designed DNA nanoflowers based on transferrin receptor aptamers, which can effectively load PROTACs and deliver them to the brain for action, achieving precise medicine for ALS patients with FUS mutations.

In view of this, in a typical specific embodiment of the present invention, a FUS proteolysis-targeting chimera is provided, the FUS proteolysis-targeting chimera having the general structure: E-F;

E is an E3 ubiquitin ligase ligand, F is an aptamer specifically binding to FUS protein;

wherein the E3 ubiquitin ligase ligand can be a CRBN ligand or VHL ligand.

The FUS protein can be human-derived, which can be wild-type FUS protein or mutant FUS protein, wherein the mutant FUS protein includes FUS mutant proteins that mediate amyotrophic lateral sclerosis (including FUS-P525L, FUS-R521C, FUS-R521G, and FUS-R521H).

Nucleotide sequences of the aptamers specifically binding to FUS protein are shown in SEQ ID NOs: 1-5. further preferably as shown in SEQ ID NO: 1.

The present invention also performed a series of modifications on the above aptamers, the modifications can be chemical modifications, these chemical modifications are well-known to those skilled in the art, such as phosphorothioate (PS) modification, through these chemical modifications, the serum stability and affinity of the aptamers can be effectively improved. Further, the phosphorothioate modification is full phosphorothioate modification, wherein the full phosphorothioate modification refers to the complete replacement of phosphate oxygen bonds with phosphorothioate bonds in the molecular structure of the aptamer.

Further, to achieve the connection between the aptamer and the E3 ubiquitin ligase ligand, the aptamer (5' terminus) is modified with an azide group, the E3 ubiquitin ligase ligand is modified with an alkyne group, and the two are coupled through click chemistry reaction.

Wherein, the alkyne group-modified E3 ubiquitin ligase ligand can be an alkyne group-modified CRBN ligand or an alkyne group-modified VHL ligand;

the alkyne group-modified CRBN ligand is a thalidomide-based CRBN ligand (thalidomide-O-amido-propargyl), its structural formula is:

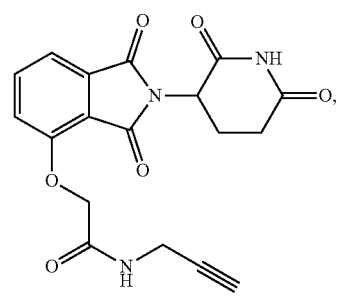 [SMILES: C#CCNC(=O)COc1cccc2c1C(=O)N(C1CCC(=O)NC1=O)C2=O]

this compound and its preparation method have been disclosed in Chinese Patent application CN 116179554 A, which will not be repeated here.

The alkyne group-modified VHL ligand is alkyne group-modified VH032 (VH032-propargyl, CAS No.: 2098799-78-9), its structural formula is:

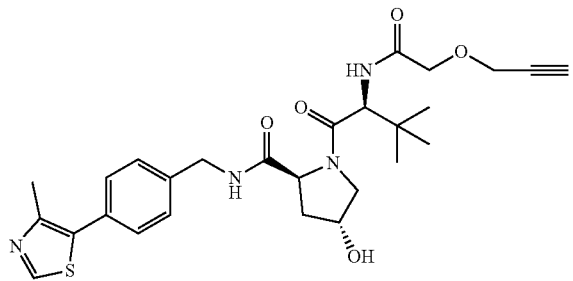 [SMILES: C#CCOCC(=O)N[C@H](C(=O)N1C[C@H](O)C[C@H]1C(=O)NCc1ccc(-c2scnc2C)cc1)C(C)(C)C]

This compound can be obtained commercially.

In another specific embodiment of the present invention, a method for preparing the above FUS proteolysis-targeting chimera is provided, wherein the method comprises:

synthesizing single-stranded RNA with azide modification and terminally alkyne-modified E3 ubiquitin ligase ligand, and coupling the single-stranded RNA with azide modification and the terminally alkyne-modified E3 ubiquitin ligase ligand through click reaction.

Further, the azide modification is at the 5' end of the single-stranded RNA, specifically connected to the 5' terminus of the single-stranded RNA through a C6 amino phosphoramidite monomer.

The specific reaction conditions for the click reaction coupling comprise: mixing the single-stranded RNA with azide modification and the terminally alkyne-modified E3 ubiquitin ligase ligand at a molar ratio of 1:1-10 (preferably 1:5), incubating at 30-40° C. (preferably 37° C.) for 1-10 hours (preferably 5 hours), followed by purification.

The purification includes steps such as ultrafiltration and centrifugation, such as removing excess CRBN ligand or VHL ligand through a 3K molecular weight cutoff ultrafiltration tube, which is not specifically limited herein.

In another specific embodiment of the present invention, an application of the FUS proteolysis-targeting chimera in preparing DNA nanoflowers based on transferrin receptor aptamers is provided.

In another specific embodiment of the present invention, a DNA nanoflower based on transferrin receptor aptamers is provided, wherein the DNA nanoflower is loaded with the above FUS proteolysis-targeting chimera. Specifically, the DNA nanoflower utilizes transferrin receptor-targeting aptamers and rolling circle amplification technology to penetrate the blood-brain barrier, while using base complementarity principles to load the FUS proteolysis-targeting chimera onto the DNA nanoflower carrier, thereby delivering the FUS proteolysis-targeting chimera to the brain to degrade wild-type and mutant FUS proteins to alleviate and treat amyotrophic lateral sclerosis.

Specifically, the method for preparing the DNA nanoflower based on transferrin receptor aptamers comprises:

adding a DNA polymerase to a system containing a cyclized DNA nanoflower template and a primer for rolling circle amplification, then adding the above FUS proteolysis-targeting chimera.

Wherein, the nucleotide sequence of the transferrin receptor aptamer is as shown in SEQ ID NO: 7.

The cyclized DNA nanoflower template contains at least sequences complementary to the transferrin receptor aptamer and the nucleotide sequence of the FUS proteolysis-targeting chimera.

The primer is as shown in SEQ ID NO: 9.

The DNA polymerase is preferably a DNA polymerase suitable for rolling circle amplification, and in a specific embodiment of the present invention, the DNA polymerase is phi29 DNA polymerase.

Wherein, the cyclized DNA nanoflower template is obtained by phosphorylating the 5' end of a linear DNA nanoflower template and cyclizing the linear DNA nanoflower template; specifically, T4 ligase can be used to cyclize the linear DNA nanoflower template.

The nucleotide sequence of the linear DNA nanoflower template is as shown in SEQ ID NO: 8.

In another specific embodiment of the present invention, applications of the above FUS proteolysis-targeting chimera or DNA nanoflower based on transferrin receptor aptamers in preparing products are provided.

The products have at least one or more of the following effects:

(a) degradation of FUS protein;
(b) treatment of amyotrophic lateral sclerosis.

Wherein, the FUS protein can be human-derived, which can be wild-type FUS protein or mutant FUS protein, wherein the mutant FUS protein includes FUS mutant proteins that mediate amyotrophic lateral sclerosis.

The effect (a) specifically manifests as: penetrating the blood-brain barrier to enter the brain, achieving brain delivery, thereby degrading brain FUS protein.

The product can be a pharmaceutical composition or an experimental reagent, wherein the experimental reagent is a common experimental reagent for non-pharmaceutical purposes, thus can be used for basic research related to the occurrence and development of amyotrophic lateral sclerosis.

In another specific embodiment of the present invention, a pharmaceutical composition is provided, wherein the pharmaceutical composition comprises as an active ingredient at least one selected from the above FUS proteolysis-targeting chimera or the DNA nanoflower based on transferrin receptor aptamers. The pharmaceutical composition can be used to degrade FUS protein and thereby treat amyotrophic lateral sclerosis.

Specifically, the pharmaceutical composition further comprises at least one pharmaceutically inactive ingredient.

The pharmaceutically inactive ingredients can be carriers, excipients, diluents, etc. commonly used in pharmacy. Moreover, according to conventional methods, it can be formulated into dosage forms such as powders, granules, suspensions, emulsions, syrups, sprays, and other oral preparations, external preparations, suppositories, and sterile injection solutions.

The carriers, excipients, diluents, and other pharmaceutically inactive ingredients that can be included are well-known in the field, and those skilled in the art can determine their compliance with clinical standards.

In another specific embodiment of the present invention, the carriers, excipients, and diluents include but are not limited to lactose, glucose, sucrose, sorbitol, mannitol, xylitol, erythritol, maltitol, starch, gum arabic, alginates, gelatin, calcium phosphate, calcium silicate, cellulose, methylcellulose, microcrystalline cellulose, polyvinylpyrrolidone, water, methylparaben, propylparaben, talc, magnesium stearate, mineral oil, etc.

In another specific embodiment of the present invention, the pharmaceutical composition of the present invention can be administered into the body through known methods, for example, through intravenous systemic delivery or local injection delivery to tissues of interest. Such administration can be carried out via single or multiple doses. Those skilled in the art understand that the actual dosage to be administered in the present invention can vary greatly depending on various factors, such as target cells, biological type or its tissues, general condition of the subject to be treated, route of administration, mode of administration.

In another specific embodiment of the present invention, the subject of pharmaceutical administration can be human and non-human animals, especially non-human mammals, such as mice, rats, guinea pigs, rabbits, dogs, monkeys, apes.

In another specific embodiment of the present invention, a method for treating amyotrophic lateral sclerosis is provided, comprising administering to a subject a therapeutically effective amount of the above FUS proteolysis-targeting chimera, DNA nanoflower based on transferrin receptor aptamers, or pharmaceutical composition.

The subject refers to an animal that is already the object of treatment, observation, or experiment, preferably a mammal, most preferably a human. The term "therapeutically effective amount" refers to the amount of active compounds or agents, including the compounds of the present invention, which can induce biological or medical responses in tissue systems, animals, or humans sought by researchers, veterinarians, doctors, or other medical personnel, including alleviation or partial alleviation of symptoms of the disease, syndrome, condition, or disorder being treated. It must be recognized that the optimal dosage and interval for administration of the active ingredients of the present invention are determined by their nature and external conditions such as the form, route, and site of administration and the specific mammal being treated, and this optimal dosage can be determined by conventional techniques. It must also be recognized that the optimal regimen, i.e., the daily dose of the compound within a specified time, can be determined by methods well-known in the art.

The following examples further illustrate the present invention in conjunction with specific examples. The following examples are only for explaining the present invention and do not limit its content. If specific experimental conditions are not noted in the examples, they are typically carried out under conventional conditions or as recommended by the sales company; unless specifically limited in the present invention, all can be obtained through commercial channels.

Example 1: Synthesis of Chimeric Molecules (1) 5' azide-modified RNA ligands were designed and synthesized, where $N_3$ azide modification was connected to the 5' terminus of RNA ligands through C6 amino phosphoramidite monomer. The nucleotide sequences of azide-modified RNA ligands (i.e., $N_3$-FUS-RNA #1~$N_3$-FUS-RNA #5) are shown in SEQ ID Nos: 1-5, and the nucleotide sequence of the control RNA ligand ($N_3$-FUS-RNA #NC) is shown in SEQ ID NO: 6. The mass spectrometry results of different azide-modified RNA ligands are shown in FIG. 1 to FIG. 6.

(2) For the PROTAC coupling reaction: azide-modified RNA aptamers were mixed with alkyne-containing CRBN ligand i.e.,

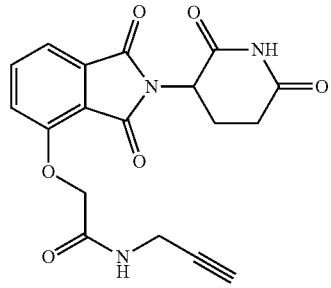 [SMILES: C#CCNC(=O)COc1cccc2c1C(=O)N(C1CCC(=O)NC1=O)C2=O]

or VHL ligand i.e.,

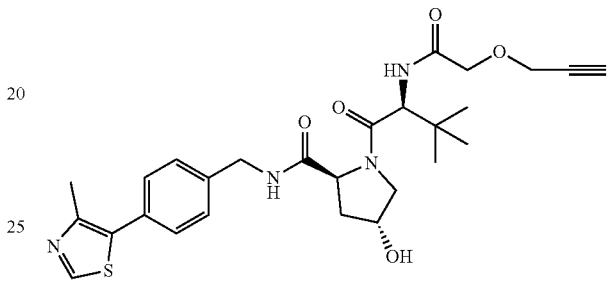

at a 1:5 molar ratio, incubated at 37° C. for 5 hours, then excess alkyne-containing CRBN ligand or VHL ligand was removed through a 3K molecular weight cutoff ultrafiltration tube, and finally the coupling reaction efficiency was detected through 20% non-denaturing SDS-PAGE gel. The results are shown in FIG. 7B, where dFUS-C1 migrated slower than FUS-1, indicating successful coupling. It should be noted that $N_3$-FUS-RNA #1 shown in FIG. 7A corresponded to FUS-1 shown in FIG. 7B, and so on. dFUS-C1 represented the PROTAC obtained by coupling FUS-1 with CRBN ligand, dFUS-V1 represented the PROTAC obtained by coupling FUS-1 with VHL ligand, and so on, thus 10 PROTACs were obtained in total.

Example 2: Testing of Degradation Performance of 10 PROTACs on FUS Protein in PC12 Cells The 10 PROTACs were transfected into PC12 cells at a final concentration of 125 nM using liposomes. After 24 hours, the cells were lysed, and changes in FUS protein were detected by Western blot. FIG. 8A to FIG. 8B show the degradation of FUS by different PROTACs in PC12 cells. dFUS-C1 was able to stably and efficiently degrade FUS protein, and was therefore selected for subsequent experiments.

Figure 9A:
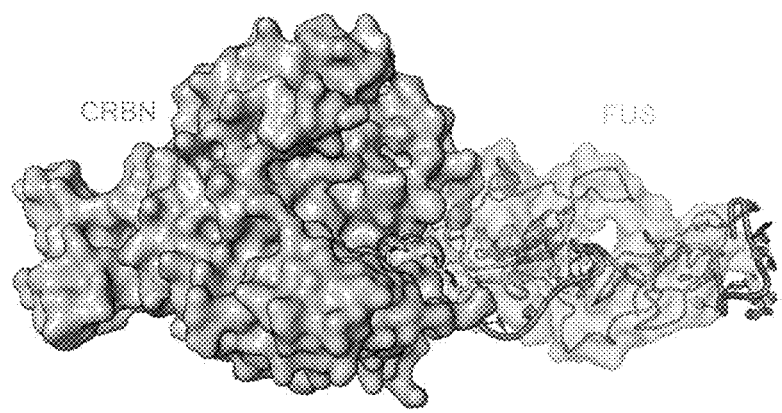
Figure 9B:
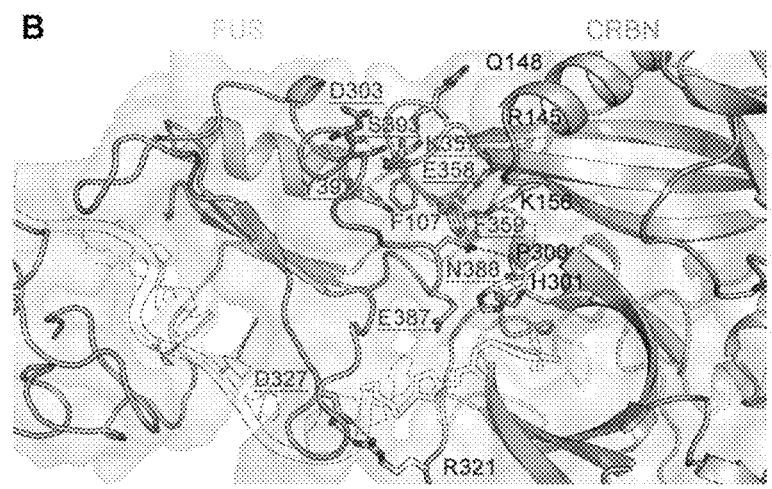
Figure 10A:
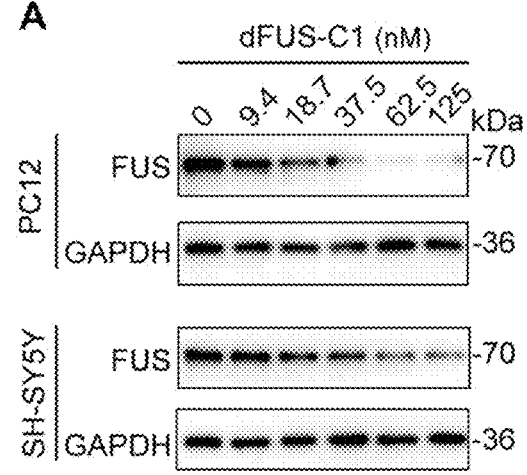
Figure 10B:
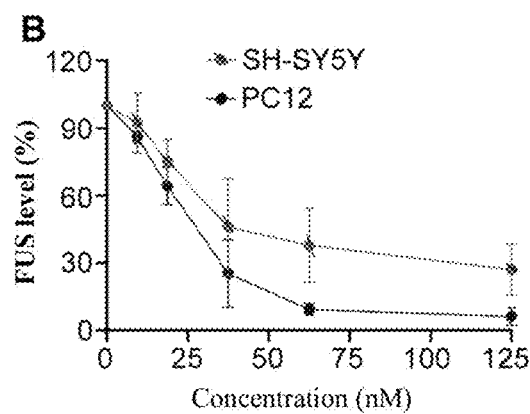
Figure 10C:
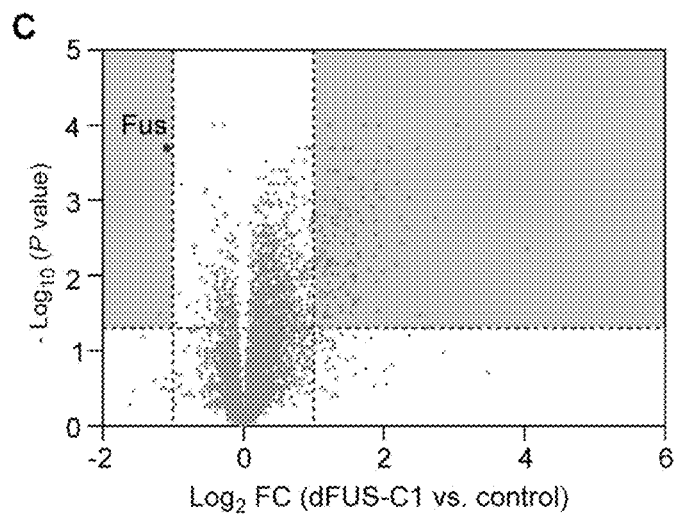
Figure 11A:
Figure 11B:
Figure 11C:
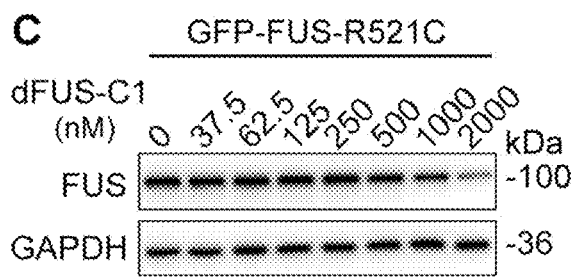
Figure 11D:
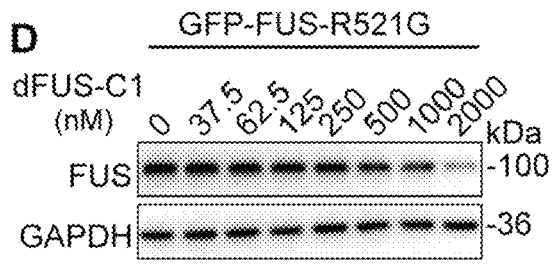
Figure 11E:
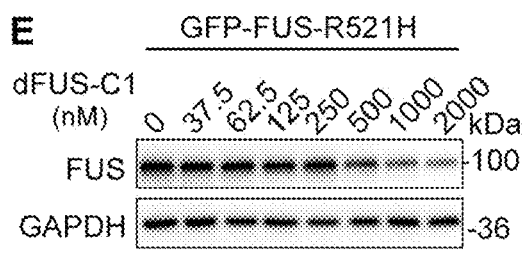

Example 3: Testing of Degradation Performance of dFUS-C1 on FUS Protein dFUS-C1 solutions were prepared at concentration gradients of 9.4 nM, 18.7 nM, 37.5 nM, 62.5 nM, and 125 nM, and were transfected into PC12 or SH-SY5Y cells using liposomes. After 24 hours, the cells were lysed, and changes in FUS protein were detected by Western blot. FIG. 9A to FIG. 9B show the molecular docking of dFUS-C1 with FUS and CRBN and the specific amino acid binding sites of dFUS-C1 with FUS and CRBN, indicating that FUS-dFUS-C1-CRBN could form a stable ternary complex. FIG. 10A to FIG. 10B show the degradation of FUS by dFUS-C1 in PC12 and SH-SY5Y cells, demonstrating that dFUS-C1 could efficiently degrade FUS protein in different cell lines. The proteomics results in FIG. 10C show that dFUS-C1 had specific degradation effects on FUS protein.

Example 4: Testing of Degradation Performance of dFUS-C1 on Mutant FUS Proteins dFUS-C1 solutions were prepared at concentration gradients of 37.5 nM, 62.5 nM, 125 nM, 250 nM, 500 nM, 1000 nM, and 2000 nM, and were transfected into 293T cells expressing different mutant FUS proteins using liposomes. After 24 hours, the cells were lysed, and changes in FUS protein were detected by Western blot. FIG. 11A to FIG. 11E show the degradation of different mutant FUS by dFUS-C1 in 293T cells. 1000 nM dFUS-C1 could efficiently degrade different forms of FUS proteins (FUS-WT, FUS-P525L, FUS-R521C, FUS-R521G, FUS-R521H).

Example 5: Cytotoxicity Testing of dFUS-C1

Figure 12A:
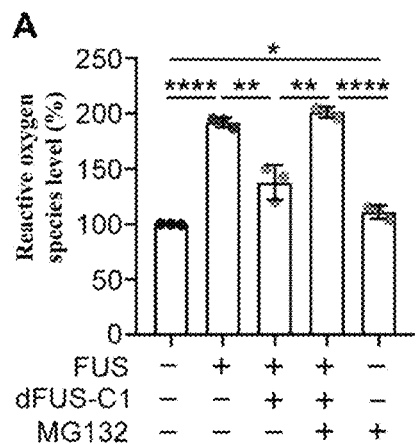
FIG. 12A~C shows the results of dFUS-C1 alleviating neurotoxicity caused by FUS overexpression in Example 5.
Figure 12B:
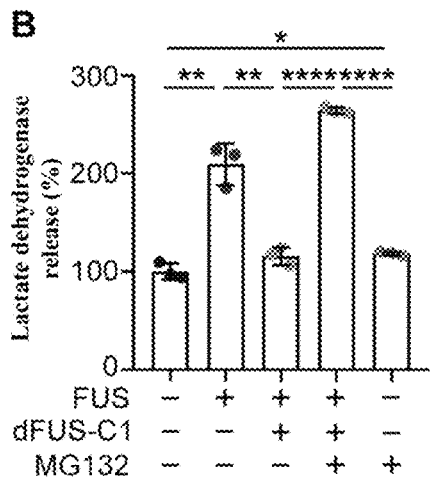
Figure 12C:
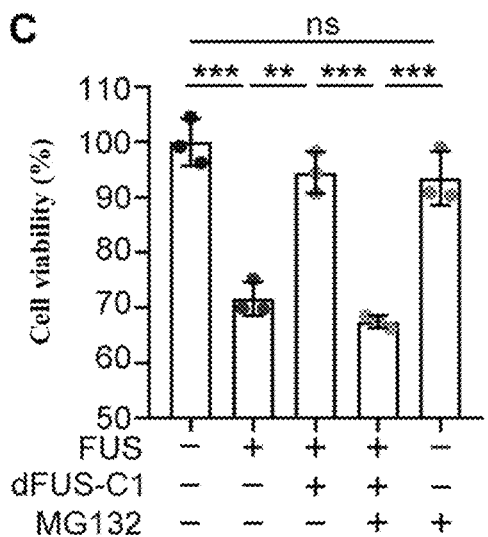

In this example, ROS detection kit, LDH release detection kit, and CCK8 reagent were used for cytotoxicity detection. Specifically: $5 \times 10^3$ SH-SY5Y cells were added to 96-well plates and cultured at 37° C., 5% $CO_2$ cell incubator for 12 hours; FUS plasmids were transfected into the wells, then the cells were cultured at 37° C., 5% $CO_2$ cell incubator for 24 hours, indicated reagents were added to each well, and corresponding indicators were detected according to the kit instructions. As shown in FIG. 12A to FIG. 12C, dFUS-C1 significantly inhibited the neurotoxicity caused by FUS overexpression.

Figure 13:
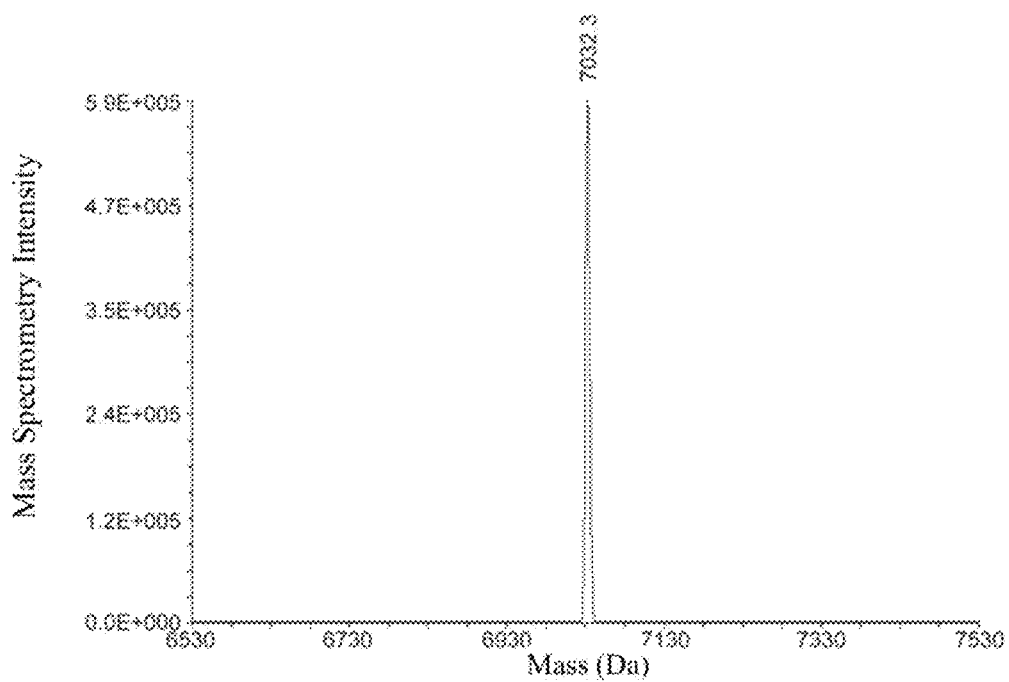
FIG. 13 shows the mass spectrometry results of dFUS-PS in Example 6.
Figure 14A:
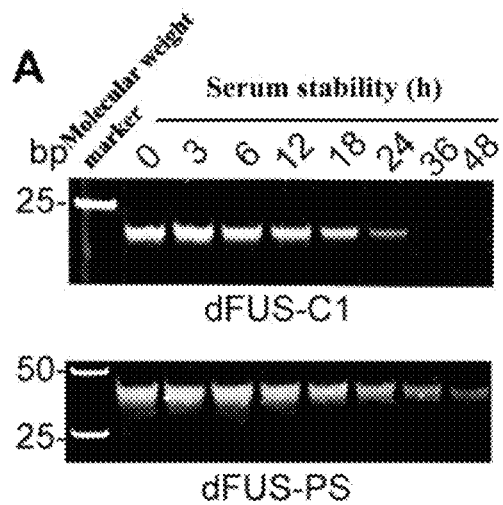
FIG. 14A~D shows the serum stability test results of dFUS-C1 and dFUS-PS and the dose-dependent FUS degradation effect of dFUS-PS in Example 6.
Figure 14B:
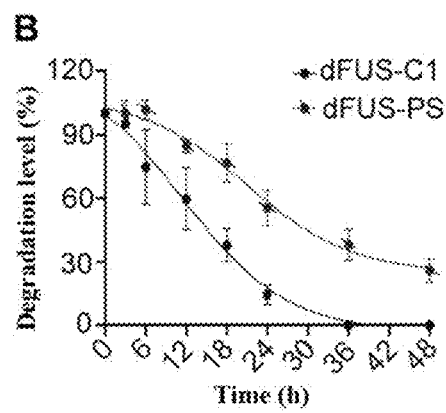
Figure 14C:
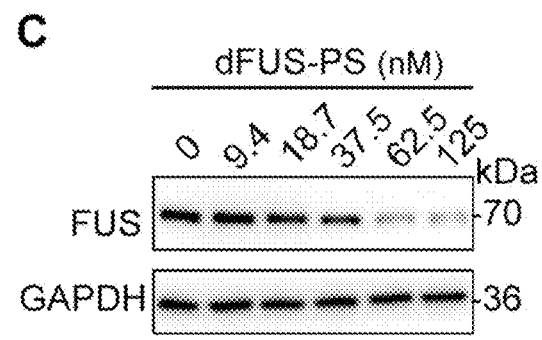
Figure 14D:
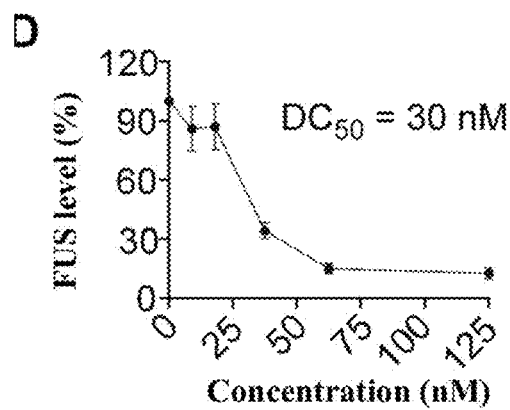

Example 6: Serum Stability Testing of dFUS-C1 and dFUS-PS and Testing of FUS Protein Degradation Performance by dFUS-PS For serum stability testing, 5 µM of dFUS-C1 or dFUS-PS (the dFUS-PS was obtained after full phosphorothioate modification of dFUS-C1, FIG. 13 shows the mass spectrometry results of dFUS-PS) was dissolved in DNEM medium containing 10% serum, incubated at 37° C., and samples were taken at indicated time points and stored at −80° C. Then 15% non-denaturing polyacrylamide gel electrophoresis was performed at 120 V for about 70 min, followed by staining with SYBR Gold nucleic acid gel stain, and finally imaged using a Bio-RAD instrument. As shown in FIG. 14A to FIG. 14B, dFUS-PS showed better serum stability than dFUS-C1. For testing the FUS protein degradation performance of dFUS-PS, dFUS-PS solutions were prepared at concentration gradients of 9.4 nM, 18.7 nM, 37.5 nM, 62.5 nM, and 125 nM, and were transfected into SH-SY5Y cells using liposomes. After 24 hours, the cells were lysed, and changes in FUS protein were detected by Western blot. As shown in FIG. 14C to FIG. 14D, dFUS-PS could still efficiently degrade FUS protein.

Example 7: Testing of Apparent Properties of DNA Nanoflowers Before and After Loading dFUS-PS DNA nanoflowers based on transferrin receptor aptamers were prepared by the following steps:
(a): Linear DNA nanoflower template and primer were synthesized using a DNA synthesizer, and the nanoflower template was modified with phosphorylation at the 5' end. The sequence information used in the preparation process is shown in Table 1.

TABLE 1

Sequence Information

| Name | Sequence (5'→3') |
|---|---|
| Transferrin receptor aptamer | GAAGGCGTGGTACCACGCTTTC (SEQ ID NO: 7) |
| FUS-RNA # 1 | GUUUGGUGAUGUUUGGUGAU (SEQ ID NO: 1) |
| Phosphorylated linear DNA nanoflower template | Pho-TGGTACCACGCCTTC<u>GTTTGGTGATGTTTGGTGAT</u>AAAAAAAAAAAAAAAAGAAAGCG (SEQ ID NO: 8) |
| Primer | AGGCGTGGTACCACGCTTTCTT (SEQ ID NO: 9) |

Figure 15:
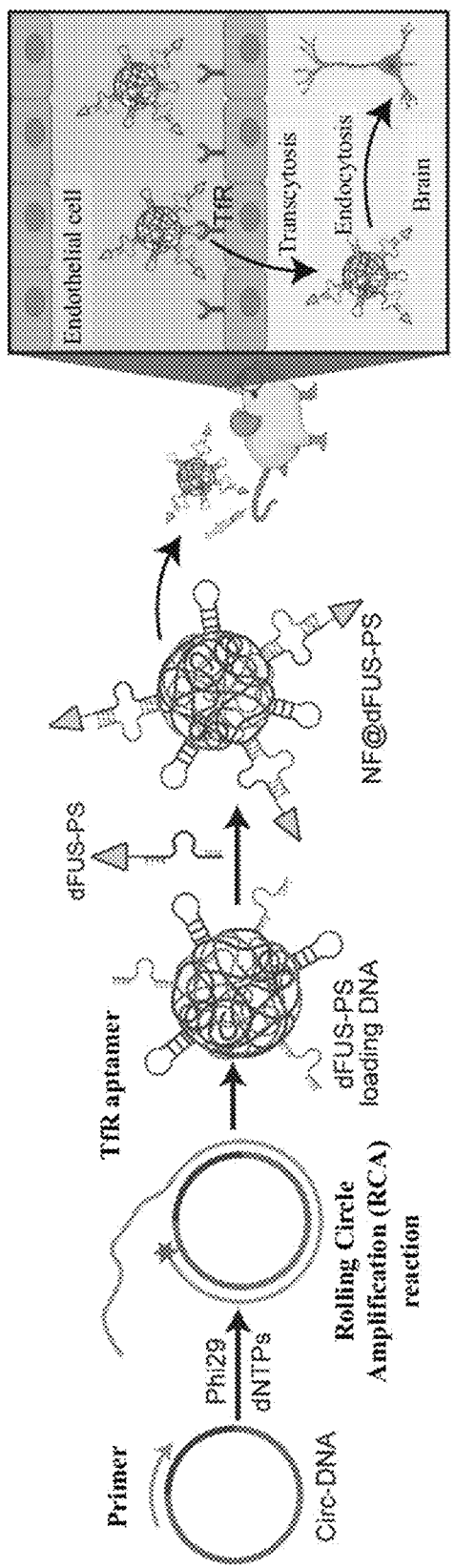
FIG. 15 shows the diagram of nanoflower synthesis, loading of dFUS-C1, and blood-brain barrier penetration mode in Example 7.

In Table 1, the phosphorylated linear DNA nanoflower template included sequences complementary to the transferrin receptor aptamer (bold English letters) and the FUS proteolysis-targeting chimera sequence (underlined letters), connected by 16 As. The nanoflower obtained through subsequent reactions contained both the transferrin receptor aptamer sequence and sequences complementary to the FUS proteolysis-targeting chimera.
(b): 5 µL T4 ligase (20 U/µL) was added to cyclize the template.
(c): 0.6 µL Phi29 enzyme (10 U/µL) and 6 µL dNTPs (10 mM) were added to a system containing cyclized template (5 µM) and primer (5 µM), reacted at 30° C. for 3 h, followed by heating at 65° C. for 10 min to inactivate the enzyme.
(d): 500 µL dd$H_2O$ was added to resuspend the product from the previous step and centrifuged at 12000 rpm for 10 min to obtain the nanoflower precipitate.
(e): The above precipitate was resuspended in 200 µL TE/$Mg^{2+}$ buffer (10 mM Tris-HCl, 12.5 mM MgCl2; pH 8), Cy5-labeled dFUS-PS (Cy5-dFUS-PS) was added to the TE/$Mg^{2+}$ buffer (10 mM Tris-HCl, 12.5 mM MgCl2; pH 8) containing nanoflowers, heated at 95° C. for 5 min, cooled naturally to room temperature, centrifuged at 12000 rpm for 10 min, and resuspended in 200 µL dd$H_2O$. Through the above steps, DNA nanoflowers loaded with dFUS-PS (NF@dFUS-PS) were successfully prepared. The modes of nanoflowers synthesis, dFUS-C1 loading and blood-brain barrier penetration are shown in FIG. 15.

Figure 16A:
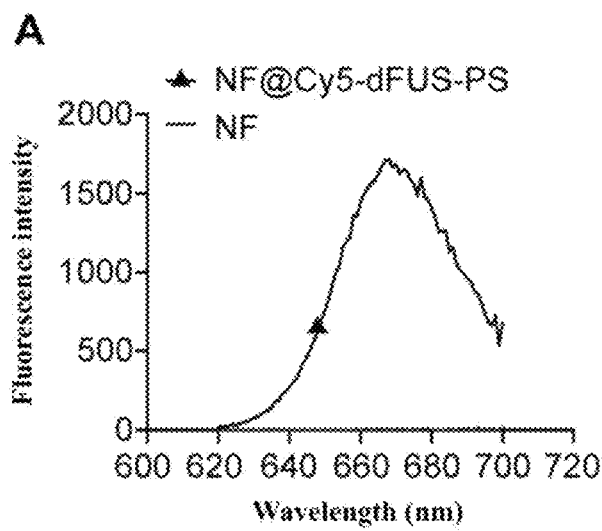
Figure 16B:
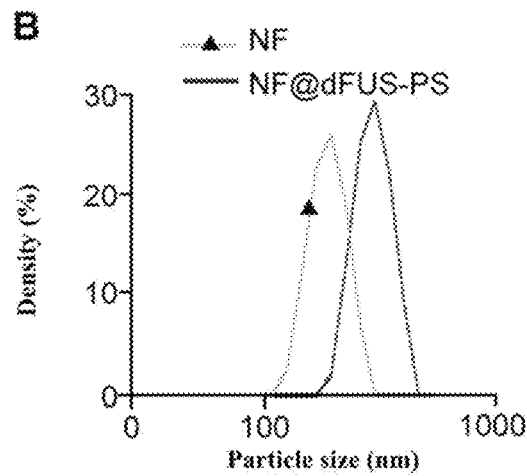
Figure 16C:
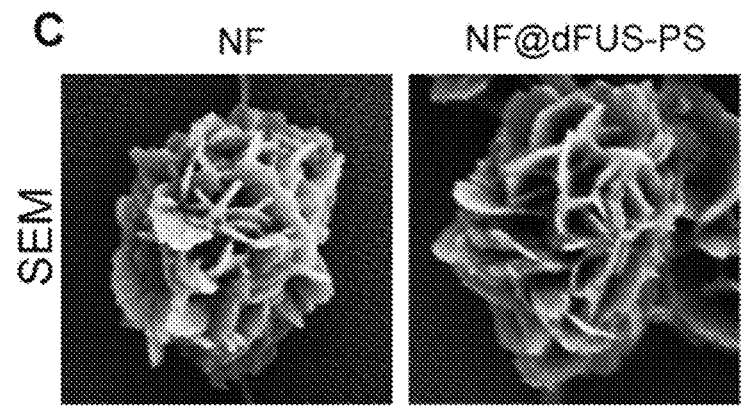

Spectral scanning at 620-700 nm was performed using a microplate reader, nanoflower particle size was measured using a nanoparticle size analyzer, and scanning electron microscopy images were taken. FIG. 16A-C shows the apparent properties of DNA nanoflowers before and after loading Cy5-dFUS-PS, wherein FIG. 16A shows the 620-700 nm fluorescence spectral scanning before and after loading PROTAC nanoflowers, FIG. 16B shows the particle size analysis before and after loading PROTAC nanoflowers, and FIG. 16C shows the scanning electron microscopy images before and after loading PROTAC nanoflowers. The above results indicated that the particle size of DNA nanoflowers increased slightly after loading Cy5-dFUS-PS without affecting the nanoflower structure.

Example 8: Testing of Blood-Brain Barrier Penetration by NF@Cy5-dFUS-PS

Figure 17A:
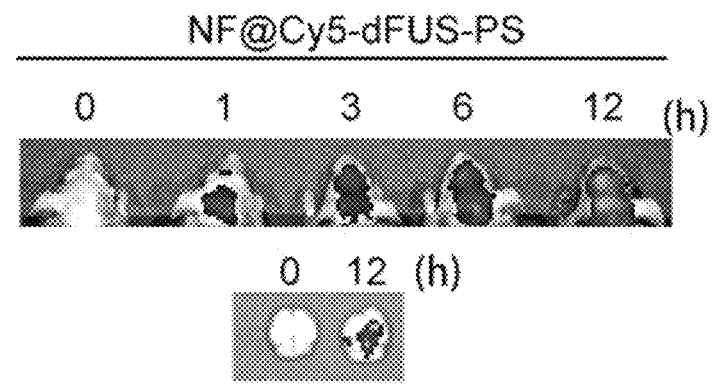
FIG. 17A~B shows the results of NF@Cy5-dFUS-PS penetrating the blood-brain barrier and entering the brain in Example 8.
Figure 17B:
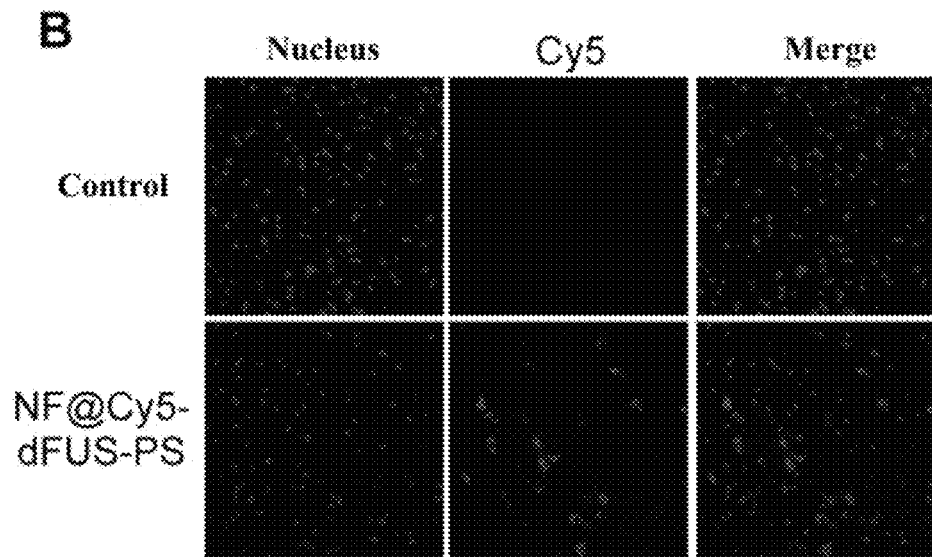

NF@Cy5-dFUS-PS was injected into BALB/C mice via tail vein, and three-dimensional in vivo imaging was performed at the indicated time points. After imaging, mouse brains were dissected, fixed, dehydrated, paraffin-embedded, sectioned, and stained with DAPI, and the sections were analyzed using a digital slice scanner. FIG. 17A to FIG. 17B demonstrate the blood-brain barrier penetration of NF@Cy5-dFUS-PS, where in vivo imaging results showed that the signal of Cy5-dFUS-PS in the brain increased over time.

Example 9: In Vivo Toxicity Testing of NF@dFUS-PS

Figure 18:
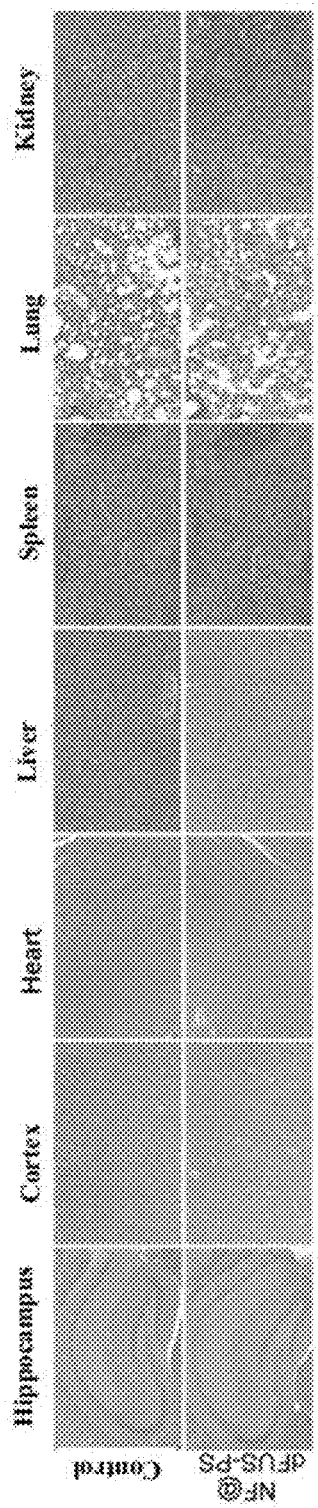
FIG. 18 shows the results of NF@dFUS-PS having no toxicity to various organs in Example 9.

NF@dFUS-PS was injected into BALB/C mice via tail vein at a dose of 10 mg/kg. After 24 hours, the brain, heart, liver, spleen, lung, and kidney were dissected, fixed, dehydrated, paraffin-embedded, sectioned, and H&E stained, and the sections were analyzed using a digital slice scanner. FIG. 18 shows the in vivo toxicity of NF@dFUS-PS, where H&E staining results indicated that NF@dFUS-PS caused no obvious morphological damage to any organs.

Figure 19:
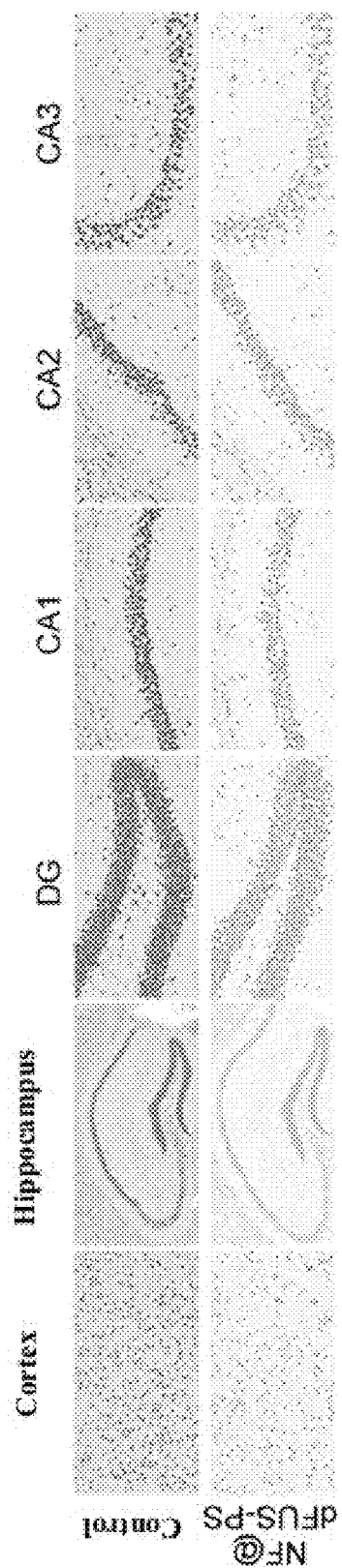
FIG. 19 shows the results of NF@dFUS-PS degrading FUS protein in mouse brain in Example 10.

Example 10: Testing of In Vivo Degradation of Mouse Brain FUS Protein by NF@dFUS-PS NF@dFUS-PS was injected into BALB/C mice via tail vein at a dose of 10 mg/kg. After 24 hours, the mouse brains were dissected, fixed, dehydrated, paraffin-embedded, sectioned, and FUS immunohistochemically stained, and the sections were analyzed using a digital slice scanner. FIG. 19 shows the results of in vivo degradation of mouse brain FUS protein by NF@dFUS-PS, where immunohistochemistry results demonstrated that NF@dFUS-PS could efficiently degrade FUS protein in the hippocampus and cortex regions of mouse brains.

The above examples were only intended to illustrate the technical concept and characteristics of the present invention, enabling those skilled in the art to understand its content and implement it accordingly, and were not intended to limit the scope of protection of the present invention. Any equivalent changes or modifications made according to the spirit of the present invention should be covered within the scope of protection of the present invention.

The invention claimed is:

1. A FUS proteolysis-targeting chimera having a general structure: E-F;
E is an E3 ubiquitin ligase ligand, F is an aptamer specifically binding to FUS protein;
wherein the E3 ubiquitin ligase ligand is a CRBN ligand, and the CRBN ligand is a thalidomide-based CRBN ligand with the structural formula:

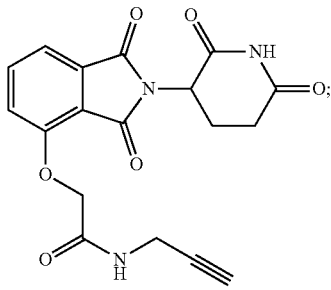 [SMILES: C#CCNC(=O)COc1cccc2c1C(=O)N(C1CCC(=O)NC1=O)C2=O]

wherein the aptamer specifically binding to FUS protein has a nucleotide sequence as shown in SEQ ID NO: 1.

2. A method for preparing the FUS proteolysis-targeting chimera according to claim 1, wherein the method comprises:
synthesizing a single-stranded RNA with azide modification and a terminally alkyne-modified E3 ubiquitin ligase ligand, and coupling the single-stranded RNA with azide modification and the terminally alkyne-modified E3 ubiquitin ligase ligand through click reaction.

3. The method according to claim 2, wherein the click reaction conditions comprise: mixing the azide-modified single-stranded RNA with the terminally alkyne-modified E3 ubiquitin ligase ligand at a molar ratio of 1:1-10, incubating at 30-40° C. for 1-10 hours, followed by purification.

4. A DNA nanoflower based on transferrin receptor aptamers, wherein the DNA nanoflower is loaded with the FUS proteolysis-targeting chimera according to claim 1.

5. The DNA nanoflower based on transferrin receptor aptamers according to claim 4, wherein a method for preparing the DNA nanoflower comprises:
adding a DNA polymerase to a system containing a cyclized DNA nanoflower template and a primer for rolling circle amplification, then adding the FUS proteolysis-targeting chimera;
wherein, the nucleotide sequence of the transferrin receptor aptamer is as shown in SEQ ID NO: 7;
wherein the cyclized DNA nanoflower template contains sequences complementary to the transferrin receptor aptamer and the FUS proteolysis-targeting chimera sequence;
the primer is as shown in SEQ ID NO: 9;
wherein the DNA polymerase is phi29 DNA polymerase.

6. A pharmaceutical composition comprising as an active ingredient at least one selected from the FUS proteolysis-targeting chimera according to claim 1 or a DNA nanoflower based on transferrin receptor aptamers;
wherein the DNA nanoflower is loaded with the FUS proteolysis-targeting chimera.

7. A pharmaceutical composition comprising as an active ingredient at least one selected from the FUS proteolysis-targeting chimera according to claim 1 or a DNA nanoflower based on transferrin receptor aptamers;
wherein the DNA nanoflower is prepared by a method comprising:
adding a DNA polymerase to a system containing a cyclized DNA nanoflower template and a primer for rolling circle amplification, then adding the FUS proteolysis-targeting chimera;
wherein, the nucleotide sequence of the transferrin receptor aptamer is as shown in SEQ ID NO: 7;
wherein the cyclized DNA nanoflower template contains sequences complementary to the transferrin receptor aptamer and the FUS proteolysis-targeting chimera sequence;
the primer is as shown in SEQ ID NO: 9;
wherein the DNA polymerase is phi29 DNA polymerase.

* * * * *